(12) United States Patent  
Devereux et al.

(10) Patent No.: US 9,216,258 B2  
(45) Date of Patent: Dec. 22, 2015

(54) APPARATUS FOR ACCURATELY CONTROLLING NEEDLE EXTENSION

(75) Inventors: Paul David Devereux, Dublin (IE); Shay Joseph Lavelle, Limerick (IE); John Neilan, Galway (IE)

(73) Assignee: Cook Medical Technologies, LLC, Bloomington, IN (US)

( * ) Notice: Subject to any disclaimer, the term of this patent is extended or adjusted under 35 U.S.C. 154(b) by 782 days.

(21) Appl. No.: 13/441,368

(22) Filed: Apr. 6, 2012

(65) Prior Publication Data

US 2012/0265156 A1    Oct. 18, 2012

Related U.S. Application Data

(60) Provisional application No. 61/474,459, filed on Apr. 12, 2011.

(51) Int. Cl.
```
A61M 5/46     (2006.01)
A61B 17/34    (2006.01)
A61M 5/32     (2006.01)
A61B 17/00    (2006.01)
A61B 19/00    (2006.01)
```
(52) U.S. Cl.
CPC .............. *A61M 5/46* (2013.01); *A61B 17/3478* (2013.01); *A61B 2017/00269* (2013.01); *A61B 2019/304* (2013.01); *A61B 2019/462* (2013.01); *A61B 2019/5425* (2013.01); *A61B 2019/5437* (2013.01); *A61M 2005/3228* (2013.01)

(58) Field of Classification Search
CPC .......... A61M 5/46; A61M 2025/0008; A61M 25/0009; A61M 5/178; A61M 5/2033; A61M 2005/3118; A61M 5/34; A61M 5/343; A61M 2205/073; A61M 2005/1452; A61M 5/322; A61B 17/3478
USPC .................................................. 604/198, 256
See application file for complete search history.

(56) References Cited

U.S. PATENT DOCUMENTS

```
5,071,424    A  * 12/1991  Reger ........................... 606/159
2006/0041270 A1 *  2/2006  Lenker et al. ................ 606/198
2010/0094216 A1 *  4/2010  Yue et al. ..................... 604/117
2010/0137810 A1 *  6/2010  Chandrasekaran et al. .. 604/198
```

OTHER PUBLICATIONS

International Preliminary Report on Patentability for International Application No. PCT/US2012/032671, Date of Issuance of Report: Oct. 15, 2013.

* cited by examiner

*Primary Examiner* — Kami A Bosworth  
*Assistant Examiner* — Hamza Darb  
(74) *Attorney, Agent, or Firm* — Brinks Gilson & Lione

(57) ABSTRACT

Devices are illustrated which provide for accurately controlling the extension of a needle from a protective sheath to increase accuracy and improve the outcome of the treatment procedure.

19 Claims, 15 Drawing Sheets

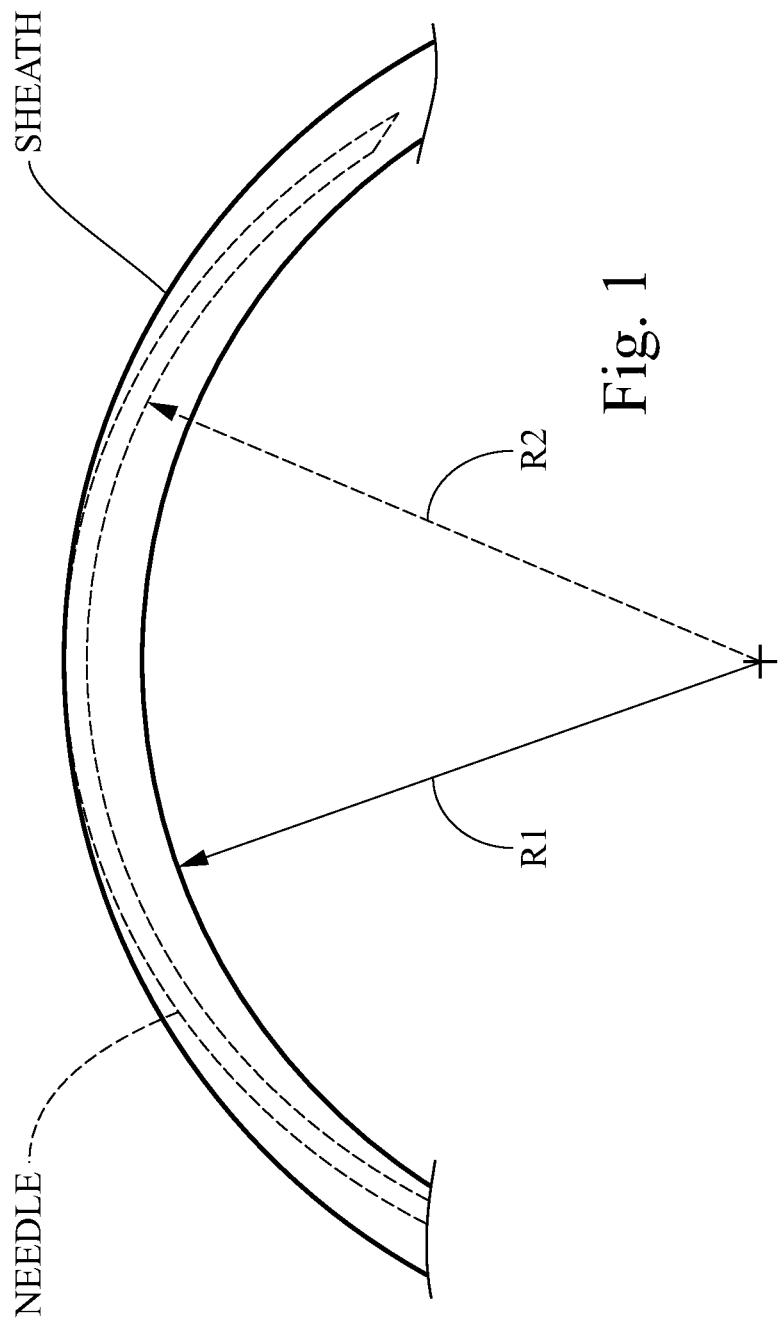

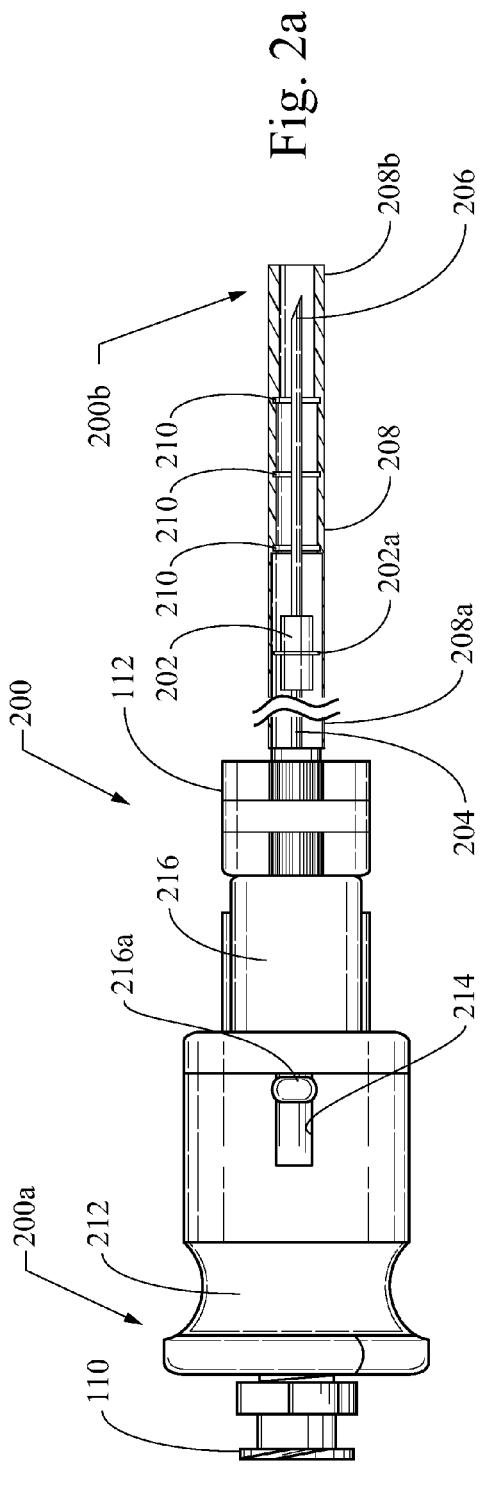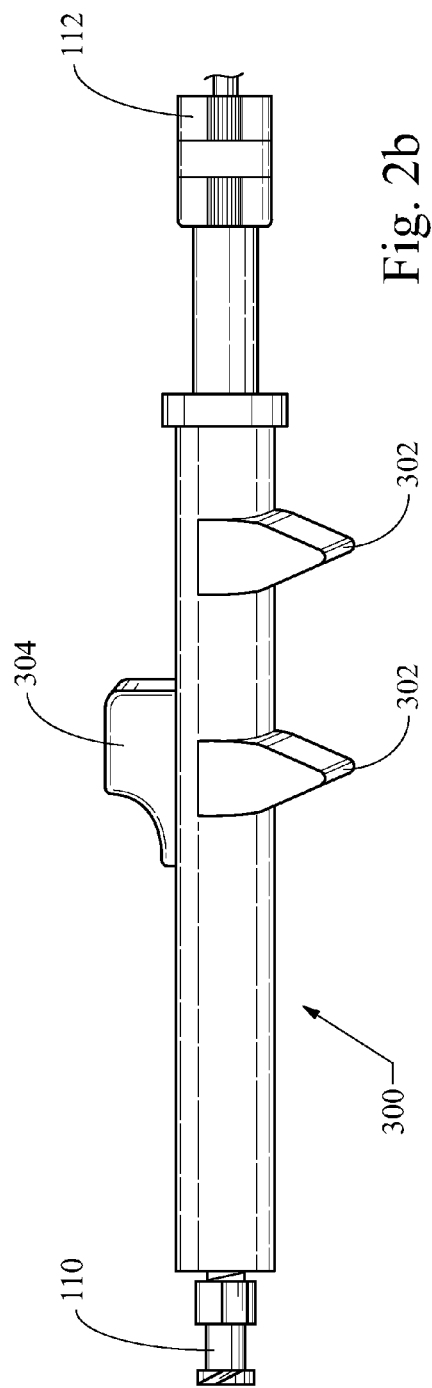

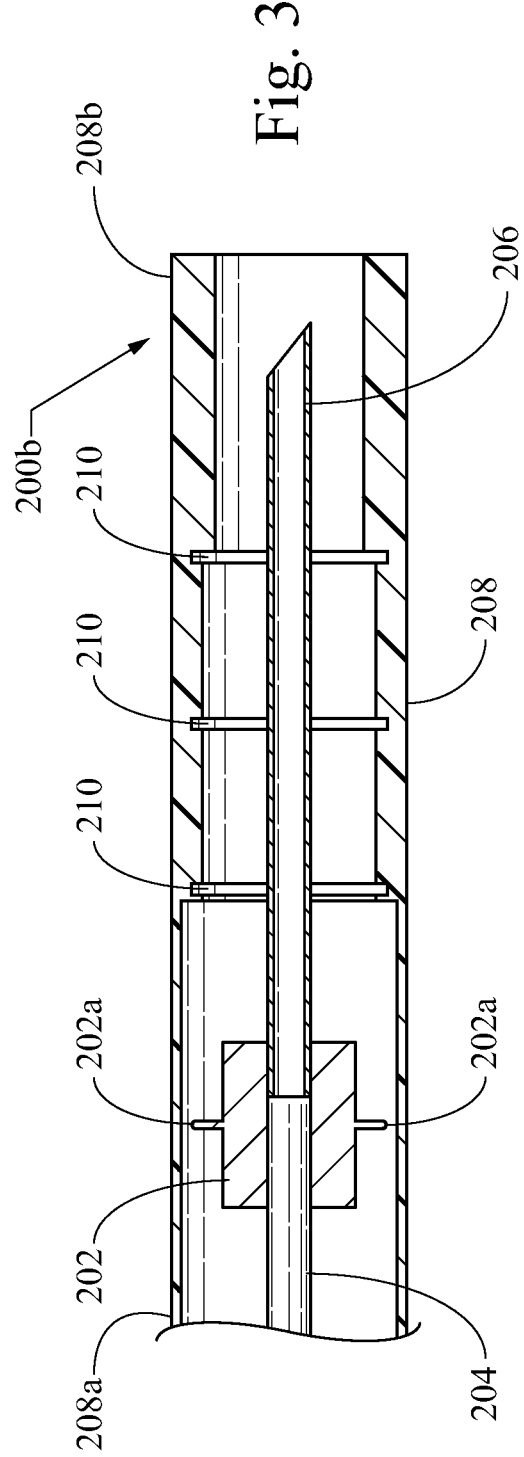

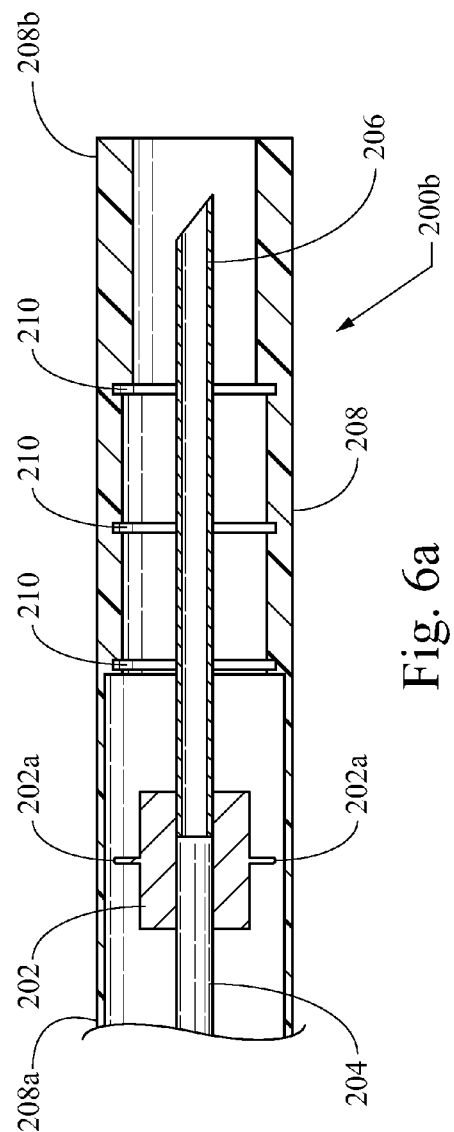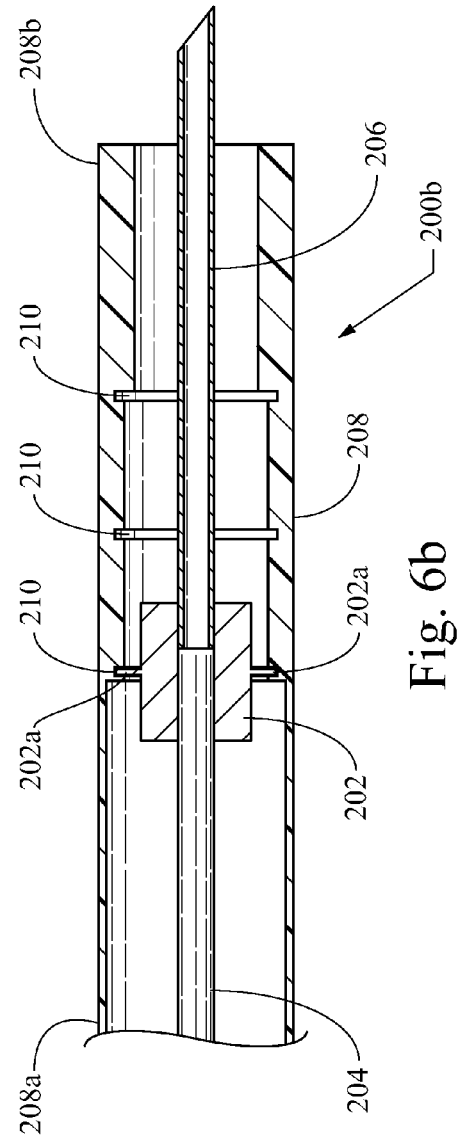

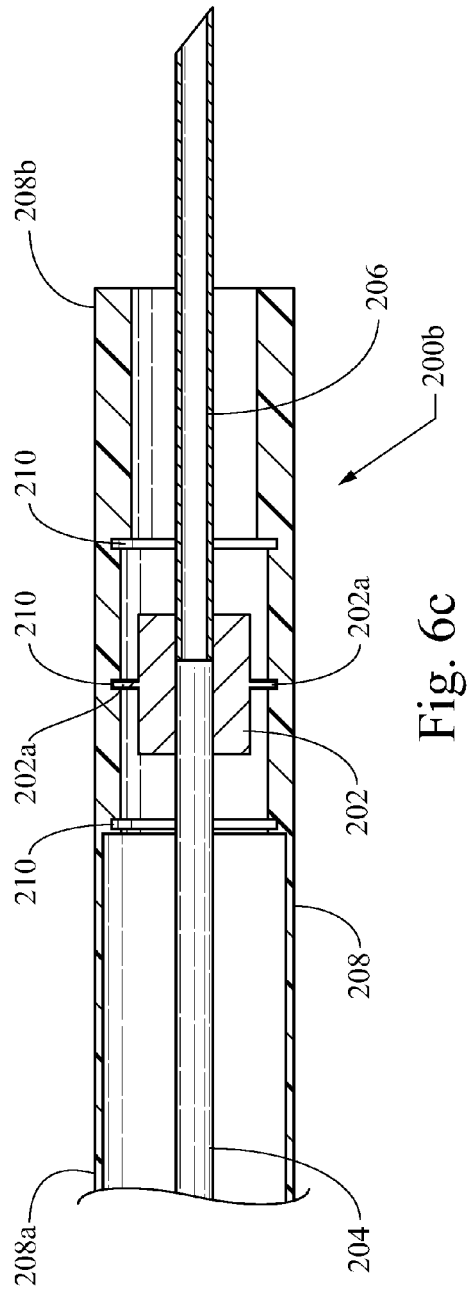
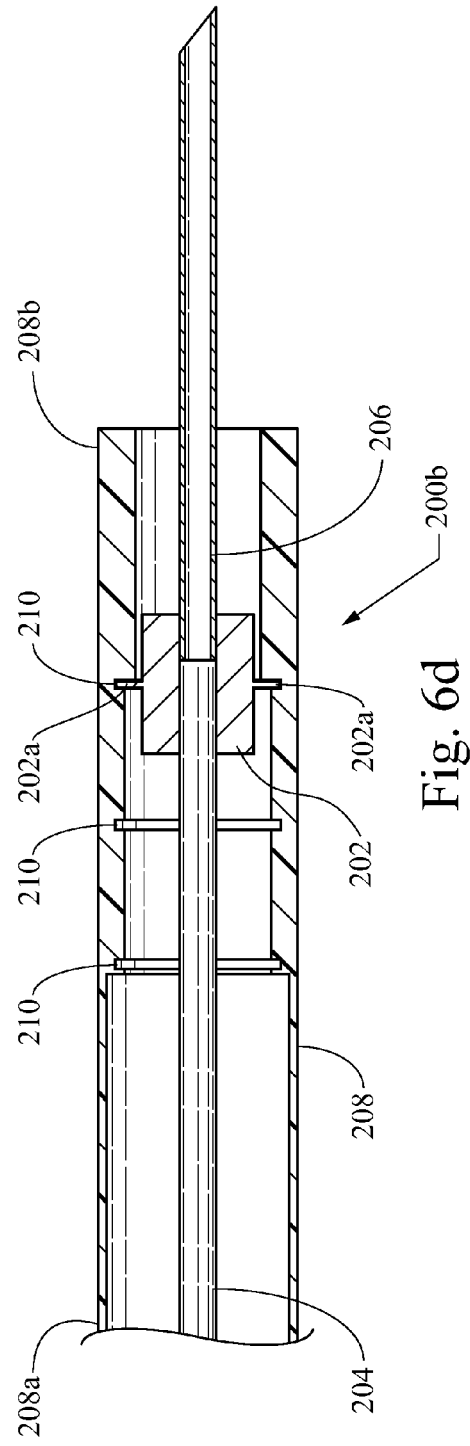

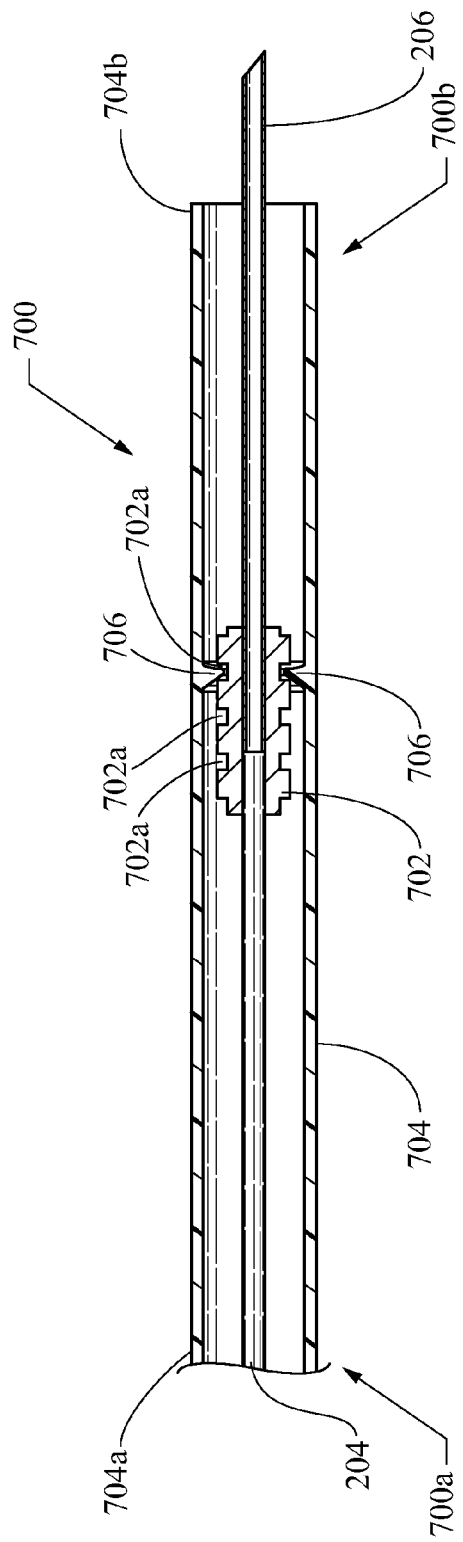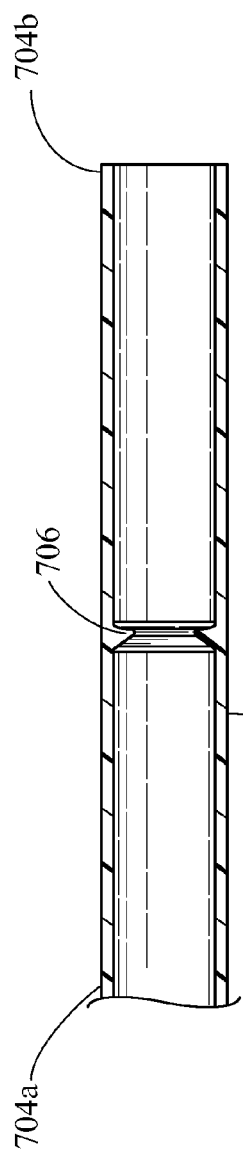
Fig. 7
Fig. 8

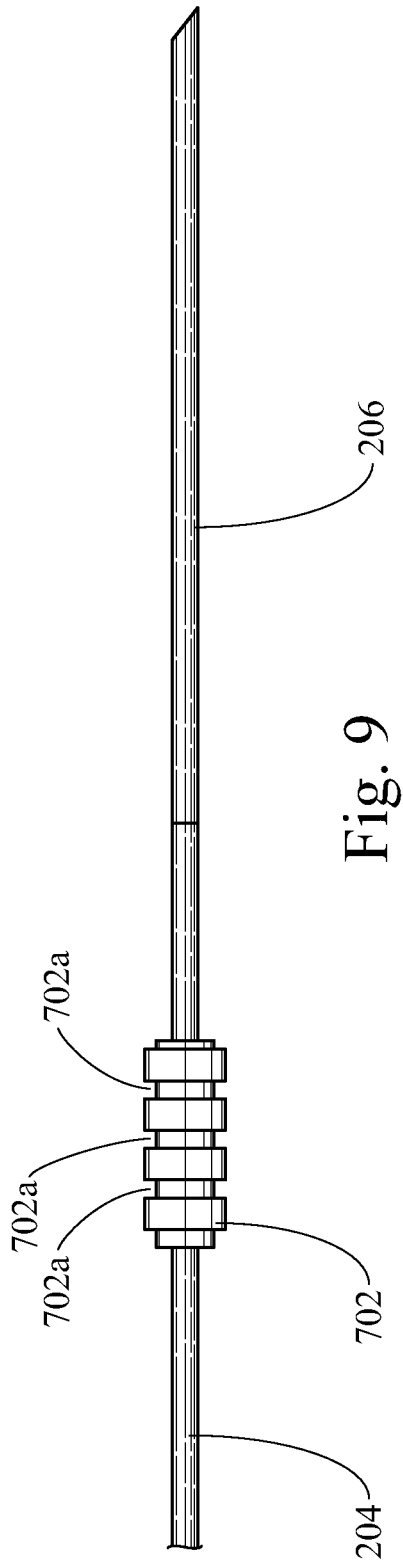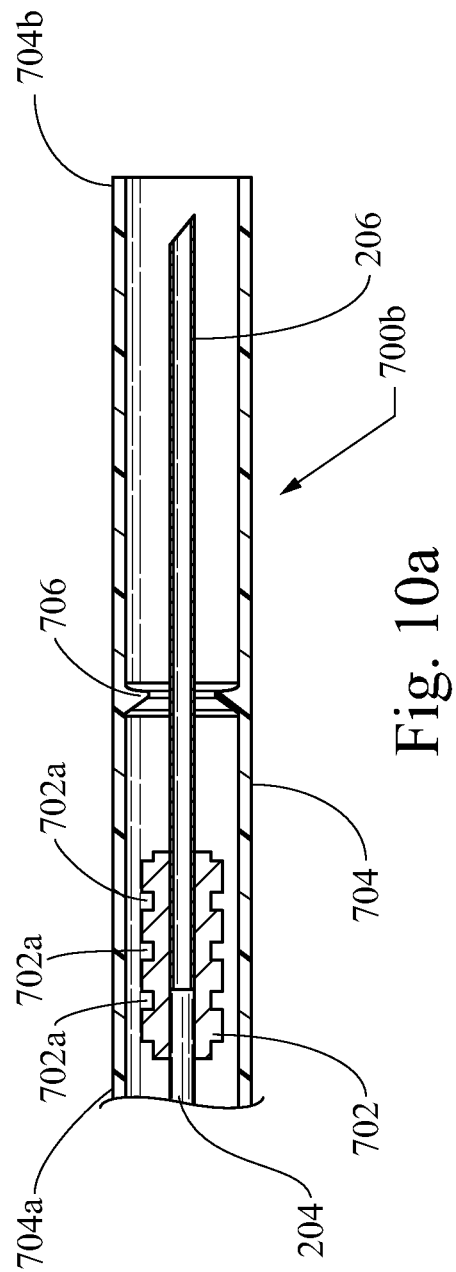

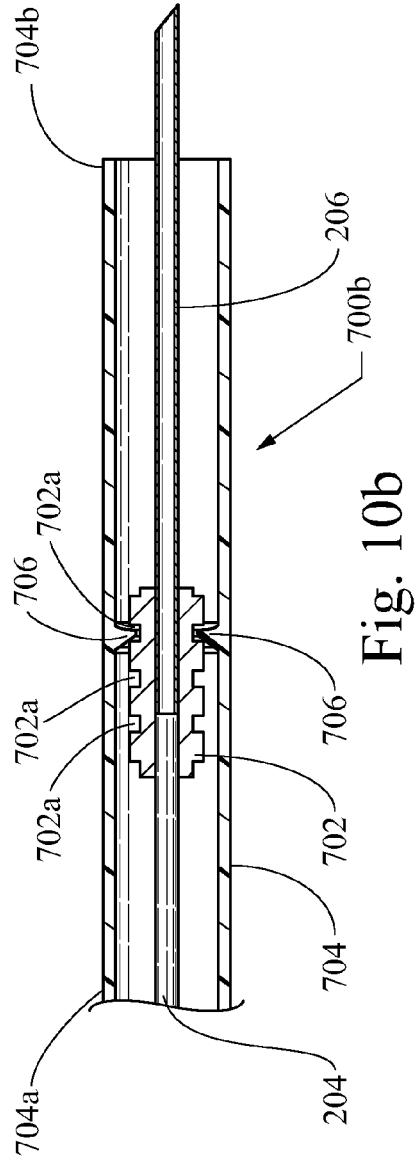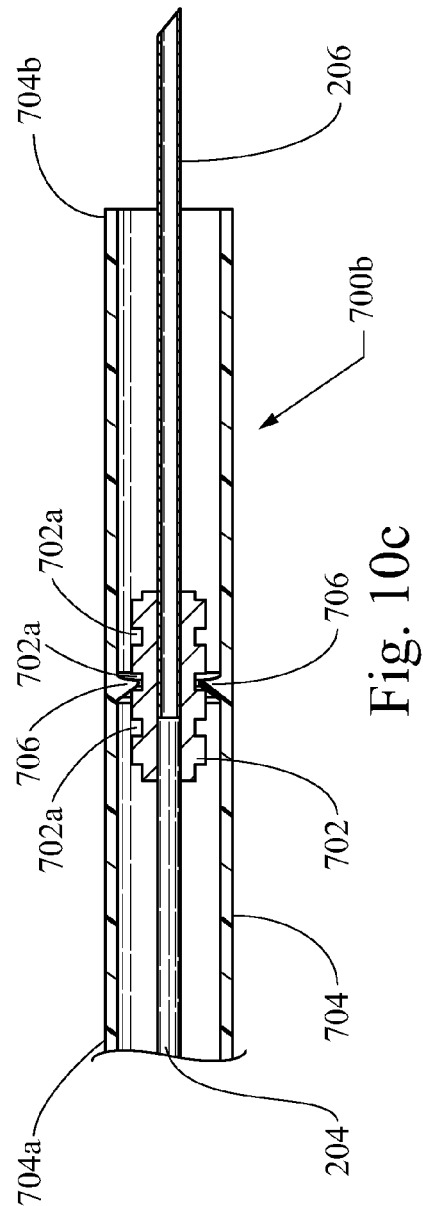

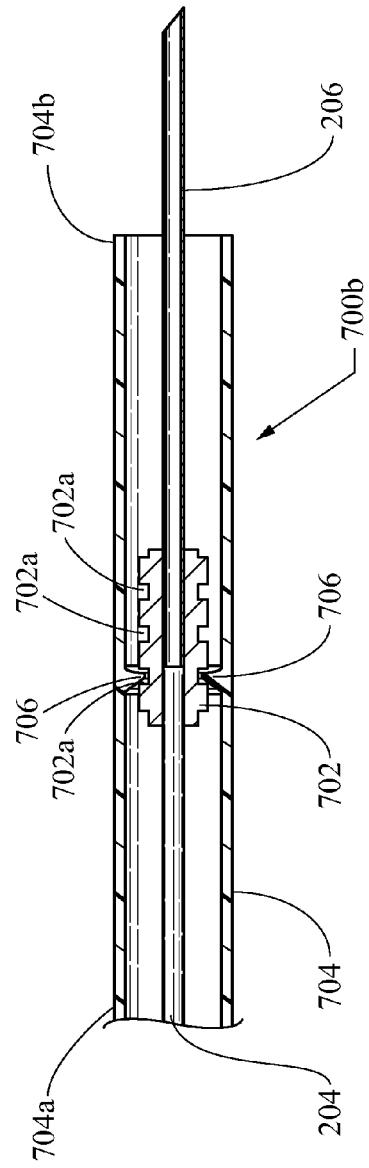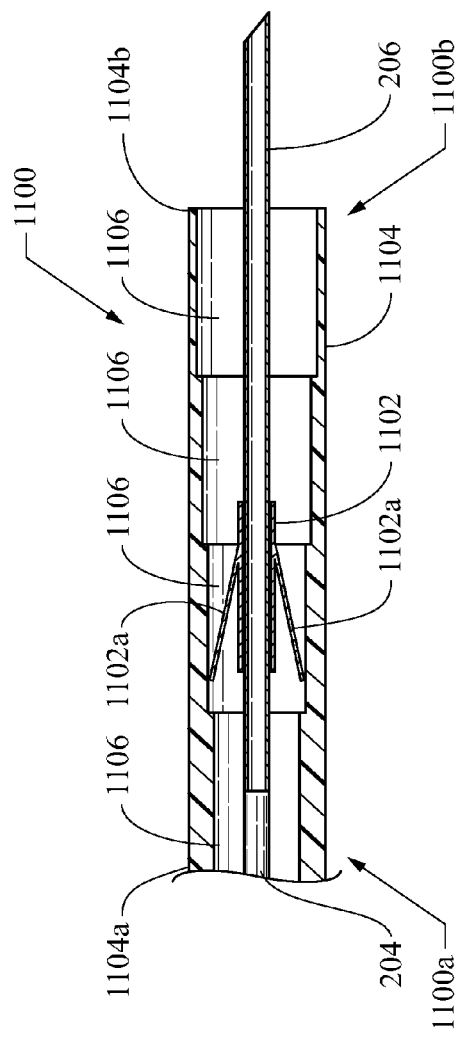

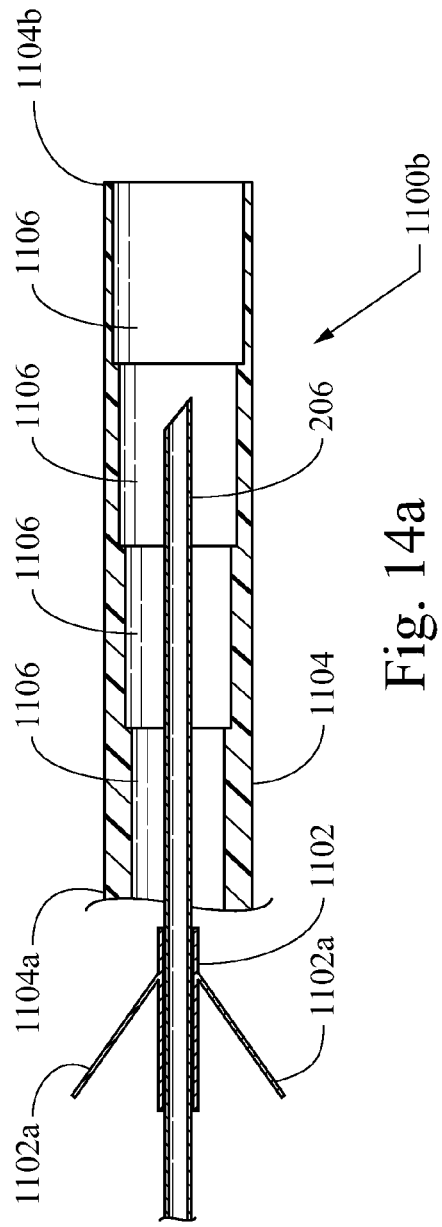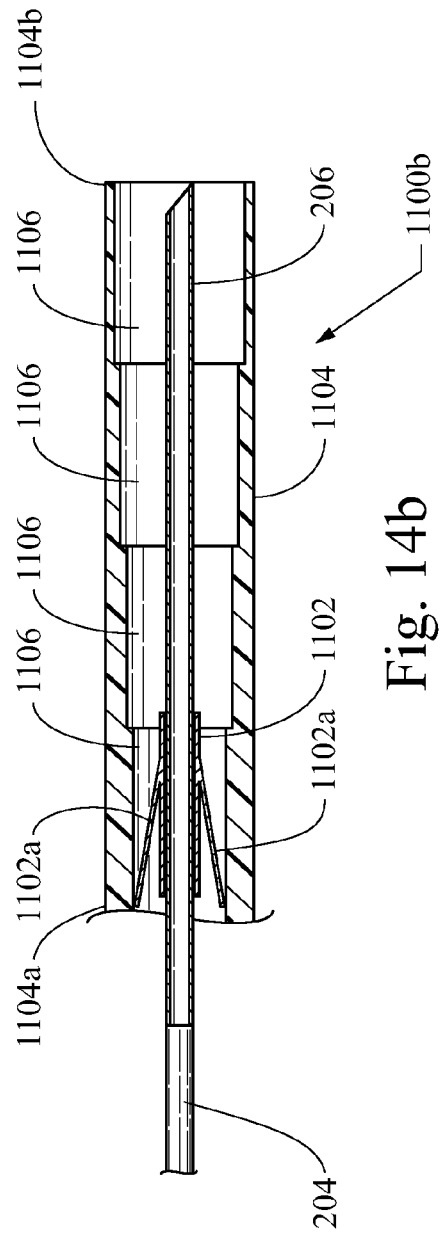
Fig. 14a
Fig. 14b

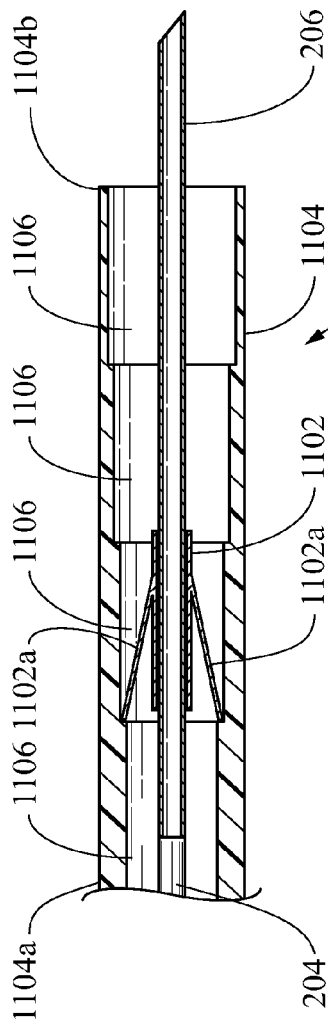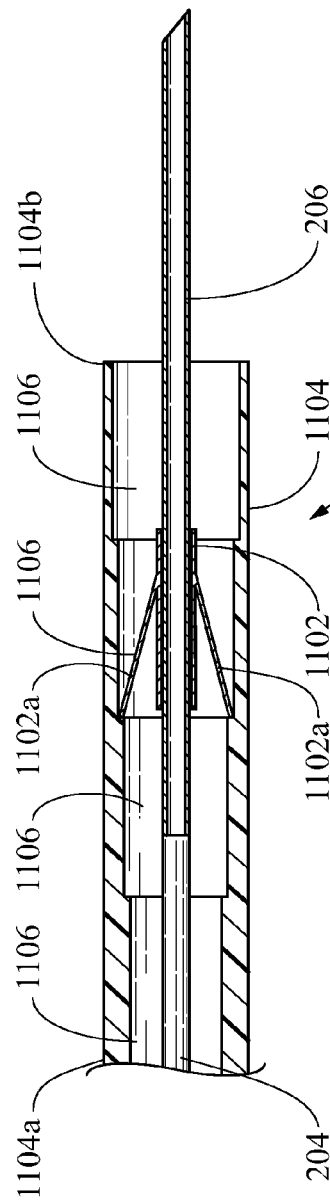
Fig. 14c
Fig. 14d

APPARATUS FOR ACCURATELY CONTROLLING NEEDLE EXTENSION

CROSS-REFERENCE TO RELATED APPLICATIONS

This application claims priority under to U.S. Provisional Application No. 61/474,459, filed on Apr. 12, 2011, the entirety of which is hereby fully incorporated by reference herein.

TECHNICAL FIELD

The present invention relates to medical devices and more specifically, needles.

BACKGROUND

Numerous medical procedures require the use of a sheathed needle, that when unsheathed, is used to pierce tissue at a certain depth for delivery of a fluid. For example, Botulinum toxin (trade name Botox®) may be injected into a bladder wall to treat an over-active bladder. Other treatments using sheath-covered needles include those in the field of urology, such as vesicoureteral reflux (VUR) as well as those in the field of gastrointestinal endoscopy such as injection into the gastrointestinal mucosa.

The needle is sheathed as it is moved to the injection location to protect the patient, endoscope, cystoscope, or other medical device from accidental piercing whilst the needle is being positioned over the target injection site. The sheath is then retracted exposing a portion of the needle. However, current devices are unable to provide for precise needle exposure which is often desired for delivery of a fluid into the area to be treated. The farther away the controlling handle is from the tip, the more pronounced this inability to accurately control component movement becomes, especially when the device is held in a curved orientation. Thus, although a user believes s/he is unsheathing, for example, 2 mm of the needle, the actual amount of needle unsheathed is not 2 mm when the device is held in a curved orientation. Instead, the unsheathed portion of the needle may be greater than or less than that desired due to material tolerances and material flexibility—but those tolerances and flexibility are often desired to properly position the device over the target injection site.

BRIEF SUMMARY

In a first aspect, a medical device is provided having a needle having a proximal portion and a distal portion, wherein the distal portion of the needle includes a sharpened tip; a sheath having a proximal portion, a distal portion, and a lumen extending between the proximal portion and the distal portion of the sheath, the lumen being defined by an inner surface of the sheath, wherein at least a portion of the needle is movably disposed through the lumen of the sheath; a plurality of spaced apart first engagement members affixed to one of the needle or the inner surface of the sheath; a second engagement member affixed to the other of the needle or the inner surface of the sheath, wherein the second engagement member is configured to releasably engage each of the first engagement members to provide incremental movement of the sheath relative to the needle.

In a second aspect, a medical device is provided having a needle having a proximal portion and a distal portion, wherein the distal portion of the needle includes a sharpened tip; a sheath having a proximal portion, a distal portion, and a lumen extending between the proximal portion and the distal portion of the sheath, the lumen being defined by an inner surface of the sheath, wherein at least a portion of the needle is movably disposed through the lumen of the sheath; an annular component disposed around a portion of a surface of the needle, wherein the annular component is configured to incrementally engage the inner surface of the sheath; and a handle attached to the sheath and the needle, where the handle is configured for axial retraction and extension of the sheath to incrementally engage the annular component and expose or conceal a distal portion of the needle.

In a third aspect, a medical device is provided having: a needle having a proximal portion and a distal portion, wherein the distal portion of the needle includes a sharpened tip; a sheath having a proximal portion, a distal portion, and a lumen extending between the proximal portion and the distal portion of the sheath, the lumen being defined by an inner surface of the sheath, wherein at least a portion of the needle is movably disposed through the lumen of the sheath; a first accurate needle extension member in communication with the inner surface of the sheath; and a second accurate needle extension member in communication with the needle, wherein the first accurate needle extension member is configured for engagement with the second accurate needle extension member for accurately extending a length of the needle from the distal portion of the sheath.

BRIEF DESCRIPTION OF THE SEVERAL VIEWS OF THE DRAWINGS

The embodiments will be further described in connection with the attached drawing figures. It is intended that the drawings included as a part of this specification be illustrative of the exemplary embodiments and should in no way be considered as a limitation on the scope of the invention. Indeed, the present disclosure specifically contemplates other embodiments not illustrated but intended to be included in the claims.

FIG. 1 illustrates the mismatched radii of curvature of sheath and needle;

FIG. 2a illustrates a partial cross-sectional side view of an exemplary device and handle for accurately controlling the extension of a needle from a protective sheath in multiple increments;

FIG. 2b illustrates an alternate side view of an exemplary handle for use with a device for accurately controlling the extension of a needle from a protective sheath;

FIG. 3 illustrates a partial cross-sectional side view of an exemplary device distal tip for accurately controlling the extension of a needle from a protective sheath in multiple increments;

FIGS. 6a-6d illustrate partial cross-sectional side views of an exemplary incremental progression of a use of an exemplary device for accurately controlling the extension of a needle from a protective sheath;

FIG. 7 illustrates a partial cross-sectional side view of an exemplary device for accurately controlling the extension of a needle from a protective sheath;

FIG. 8 illustrates a cross-sectional side view of an exemplary outer sheath;

FIG. 9 illustrates a side view of an exemplary annular component and needle;

FIGS. 10a-10d illustrate partial cross-sectional side views of an exemplary incremental progression of a use of an exemplary device for accurately controlling the extension of a needle from a protective sheath;

FIG. 11 illustrates a partial cross-sectional side view of an exemplary device for accurately controlling the extension of a needle from a protective sheath;

FIGS. 14a-14e illustrate partial cross-sectional side views of an exemplary incremental progression of a use of an exemplary device for accurately controlling the extension of a needle from a protective sheath;

DETAILED DESCRIPTION OF PRESENTLY PREFERRED EMBODIMENTS

Figure 4:
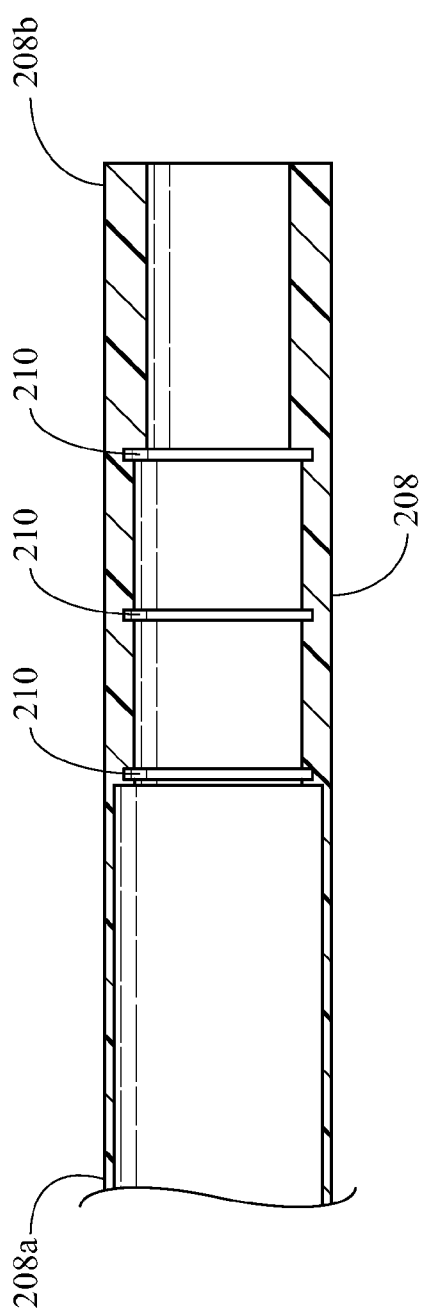
FIG. 4 illustrates a cross-sectional side view of an exemplary outer sheath.

The exemplary embodiments illustrated herein provide exemplary apparatuses for accurately controlling the extension of a needle from a protective sheath and optionally providing direct visualization of needle depth penetration. The present invention is not limited to those embodiments described herein, but rather, the disclosure includes all equivalents. Moreover, the embodiments illustrated herein can be used in the fields of urology and gastrointestinal endoscopy as well as any other field, and they are not limited to the size or shapes illustrated herein. Indeed, the devices can be used in any field where precise control of the movement of components relative to each other is desired and can be sized, manufactured, altered, or changed for the particular treatment needed.

A more detailed description of the embodiments will now be given with reference to FIGS. 1-16. Throughout the disclosure, like reference numerals and letters refer to like elements. The present disclosure is not limited to the embodiments illustrated; to the contrary, the present disclosure specifically contemplates other embodiments not illustrated but intended to be included in the claims.

Typical retractable sheath needle devices fail to provide precise needle exposure needed for treating certain ailments, such as over-active bladder, wherein a precise portion of the needle needs to pierce the subject tissue. Their handles typically include preset control positions, whereby the needle sheath can be retracted, thus controlling, although imprecisely, the exposure of needle tip. Some refer to this inability to accurately control sheath retraction (and thus, needle exposure length) as "play." Typical retractable sheath needle devices are unable to provide precise needle exposure despite having preset control positions on their handle when in a non-straight orientation, such as a curved orientation. For example, if a typical retractable sheath needle device is held in a curved orientation, the ability for it to provide the user with accurate needle extension length diminishes because there exists a certain amount of clearance between the inner diameter of the sheath and the outer diameter of the flexible needle. The clearance is desired to ensure that that the sheath can retract over the flexible needle without any dimensional interference when in a curved orientation. The clearance is also desired because it provides a pathway for ethylene oxide (EtO) sterilization.

FIG. 1 illustrates the mismatched radii of curvature of a sheath and a needle for a typical retractable sheath needle device. The farther away the controlling handle is from the tip, the more pronounced the inability to accurately control component movement becomes, especially when the device is held in a curved orientation. Thus, although a user believes s/he is unsheathing, for example, 2 mm of the needle, the actual amount of needle unsheathed is not 2 mm when the device is held in a curved orientation. Instead, the unsheathed portion of the needle may be greater than or less than that desired due to material tolerances and material flexibility—but those tolerances and flexibility are often desired to properly position the device over the target injection site.

More particularly, the movement of the needle to sheath results in a mismatch of the radii of curvature of both tubings. As can be seen in FIG. 1, when the sheath is curved, the needle does not curve at the same rate. Thus, the radius for the needle's curvature R2 is different than that of the sheath R1. As a result of the sheath and needle bending at different rates, the needle moves within the sheath, and the curvature of both the needle and the sheath are no longer aligned. This mismatch in radii of curvature increases the distance that the sheath has to retract in order to provide the correct needle extensions at the distal portion of the retractable sheath needle device. As the handle of the typical retractable sheath needle device can only provide pre-defined distances, set by control of the sheath, the typical retractable sheath needle device cannot accurately control sheath retraction (and thus the needle tip's exposure) when the shaft of a typical retractable sheath needle device is placed in a curved orientation.

Other reasons may cause play with respect to the needle and the sheath, including but not limited to, material type, wear, and temperature. Regardless of the reason, play affects the accuracy of the portion of the needle tip exposed from the sheath and the stability of the needle.

It has been discovered that the mismatch of radii problem can be overcome and the needle stabilized throughout the procedure, without altering the flexibility of the needle and while still permitting the use of a protective sheath by the discovery of a device for accurately controlling the extension of a needle from a protective sheath having an annular component located at the distal portion of the device. Thus, the needle and sheath stay aligned, and incremental control of the device is maintained at the distal end of the device, thus solving the mismatch of the radii of curvature problem.

FIG. 2a illustrates a first embodiment of an exemplary device 200 for accurately controlling the extension of a needle from a protective sheath having an exemplary handle 212; other handles are contemplated, including but not limited to that illustrated in FIG. 2b. Device 200 includes a proximal portion 200a and a distal portion 200b. At proximal portion 200a of device 200 is handle 212 having an adaptive connection, such as female luer lock adapter (FLLA) 110, configured for receiving an optional syringe. FLLA 110 is connected to outer handle component 212. Multiple connection means are contemplated, including but not limited to, the use of a screw, adhesive, over molding, thread lock, and ultrasonic welding. Outer handle component 212 is connected to inner handle component 216 and control knob 216a that moves along the pathway channel 214; however, alternate handle configurations are contemplated, including those without control knob 216a and pathway channel 214. Inner handle component 216 is attached to an adaptive connection, such as a male luer lock adapter (MLLA) 112. FLLA 110 and MLLA 112 are manufactured using plastic injection molding, but other manufacturing techniques are contemplated as are forming MLLA and/or FLLA from other medical grade materials, including but not limited to, stainless steel. MLLA 112 connects to sheath 208, having a lumen being defined by an inner surface of the sheath. Additionally, it is contemplated, although not required that MLLA 112 can be used to attach the device to the working channel of an endoscope such that it would be locked into place and free a user's hand from holding device.

The portion of needle 206 in the proximal-most direction is flared and sandwiched between FLLA 110 and outer handle component 212, although other methods for attachment are contemplated, including but not limited to, screwing, gluing, and over molding. The portion of sheath 208 in the proximal-most direction is flared and sandwiched between inner handle component 216 and MLLA 112, although other methods for attachment are contemplated, including but not limited to, screwing, gluing, and over molding. When sheath 208 is retracted, by for example, pulling inner handle component 216 in a proximal direction, it exposes needle 206. When sheath 208 is extended/advanced by using, for example, inner handle component 216, by pushing, for example, it in a distal direction within channel 214 relative to handle 212, it conceals needle 206.

Needle 206 (and other needles illustrated below) is a 23 gauge needle, although other gauges are contemplated depending upon the needs of the patient and the area to be treated. It is contemplated that needle 206 (and other needles illustrated below) is machine ground to a desired sharpness for piercing the area to be treated, including but not limited to, skin, muscle, tissue, bone, or combination thereof. Moreover, needle 206 (and other needles illustrated below) is contemplated to being of any size and shape suitable for delivering a fluid or solid or other treatment mechanism, and it can be manufactured in whole or in part from plastic, stainless steel, or other suitable medical-grade materials, including but not limited to, echogenic and other materials that may or may not provide for direct or indirect visualization using a visualization device, including but not limited to fluoroscopy, x-ray, ultrasound, or magnetic resonance imaging (MRI).

Needle 206 (and other needles illustrated below) is a stainless steel sharpened tube about one inch long and is bonded to flexible plastic tubing. In some embodiments, the flexible tube is constructed to be sufficiently flexible to assist with positioning and maintaining the scope in an angulated or deflected state. Accordingly, it is preferred that the device be flexible such that it does not unduly diminish or excessively hinder scope angulation. Other configurations and materials are contemplated depending upon the needs of the patient and the area to be treated. Throughout, patient is not limited to being a human being, indeed animals and others are contemplated. User is contemplated throughout the disclosure as being anyone or thing capable of using the device, including but not limited to, a human being and machine.

Handle components are manufactured using plastic injection molding, although other methods are contemplated as are other materials. The overall length of device 200 is 70 cm, although other dimensions are contemplated depending upon the needs of the patient, the area to be treated, and the method utilized for positioning device 200.

A user positions device 200 having sheath 208 extended over needle 206 through a flexible endoscope, cystoscope, or other device or method for positioning a needle over a treatment area. Sheath 208 is retracted by pulling inner handle component 216 in a proximal direction relative to handle component 212, thereby exposing desired depth of needle 206 as determined by annular component 202 (illustrated in FIGS. 4-6d and described below). An optional syringe is attached to FLLA 110, needle 206 is pushed into tissue to the desired depth as determined by annular component 202, and the substance is injected as needed.

FIG. 2b illustrates an alternate side view of an exemplary handle 300 for use with a device for accurately controlling the extension of a needle from a protective sheath. Handle 300 includes an adaptive connection, such as female luer lock adapter (FLLA) 110, configured for receiving an optional syringe. Finger grip 302 provides a place for a user to place an index (or other finger) there between, to provide stability to handle 300. Slider 304 is in communication with a device for accurately controlling the extension of a needle from a protective sheath and provides for sheath retraction or extension thereby exposing an accurate portion of needle tip.

FIG. 3 illustrates a partial cross-sectional view of an exemplary device 200 for accurately controlling the extension of a needle from a protective sheath. As illustrated in FIG. 2a and further illustrated in FIG. 3, sheath 208 has proximal portion 208a and distal portion 208b. Sheath 208 (and other sheaths illustrated below) is made from a polymer such as fluorinated ethylene propylene (FEP) or polytetrafluoroethylene (PTFE). However, sheath 208 (and other sheaths illustrated below) can be manufactured in whole or in part from other materials, including but not limited to, stainless steel, plastic, or other suitable medical-grade materials, including but not limited to echogenic and other materials that may or may not provide for visualization using an indirect or direct visualization device, including but not limited to, fluoroscopy, x-ray, ultrasound, direct endoscopic visualization, MRI, or combination thereof. Sheath 208 (and other sheaths illustrated below) is manufactured as an insert that can be press-fit into position, although not required as other manufacturing techniques are contemplated. Sheath 208 (and other sheaths illustrated below) can be manufactured by deep drawing, although not required, so as to achieve the step change for creating slots 210.

Figure 5:
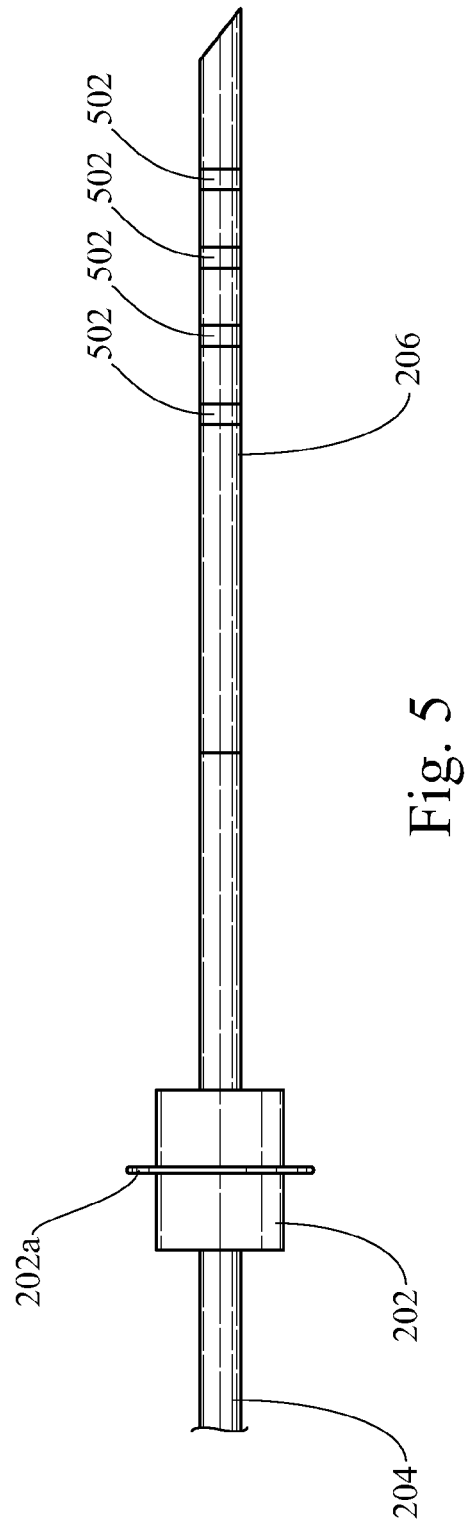
FIG. 5 illustrates a side view of an exemplary annular component and needle.

FIG. 4 illustrates a cross-sectional view of an exemplary outer sheath 208, and FIG. 5 illustrates a side view of an exemplary annular component 202 and needle 206. As further illustrated in FIGS. 4-5, along with FIG. 3, within sheath 208 is an exemplary accurate needle extension member, annular component 202, having ridge 202a that engages slots 210. Annular component 202 is attached to an exemplary accurate needle extension member, inner component 204, having a lumen extending throughout, which attaches to flexible needle 206. Annular component (and other annular components illustrated below) is made from stainless steel, however it is contemplated that it can be made from other materials, including but not limited to, metallic materials, platinum, polymers, or other materials, including but not limited to, injection molded plastic, polyether ether ketone (PEEK), or combination thereof. Annular component 202 (and other annular components illustrated below) can be attached to inner component 204 (and other inner components illustrated below) by a number of processes, including but not limited to, crimping, gluing, soldering, etc., or combination thereof.

As can be seen in FIG. 5, optional markers 502 are etched onto the surface of needle 206 and provide an additional means for providing accurate needle depth using, for example, direct endoscopic visualization at the increments of, for example, 2, 4, 6, and 8 mm such that the user knows the depth at which needle 206 penetrates the area to be treated, including but not limited to, the wall of the lower urinary tract. Markers 502 may be located elsewhere, at different positions, and in different numbers. Additionally, because markers 502 are optionally set apart at a known distance, they can also aid in measuring internal structures. Additionally, it is contemplated that markers 502 can be made from a variety of materials that provide for indirect visualization, for example, by way of ultrasound. Examples include but are not limited to having markers 502 made from Platinum-Iridium alloy or any echogenic material, including but not limited to, gold and tungsten having surface irregularities. An echogenic material includes surface irregularities that reflect ultrasonic waves and thus, allow the material to be seen with ultrasonic imaging devices. Echogenic techniques are described in U.S. Pat. No. 5,081,997 and U.S. Pat. No. 5,289,831 and are hereby incorporated by reference in their entirety. Markers 502 may be made by laser or chemical etching. It is contemplated that markers 502 can be manufactured in whole or in part from other materials, including but not limited to, stainless steel or other suitable medical-grade materials, including but not limited to, radiopaque materials, such that the material provides for visualization outside the patient using a visualization device, including but not limited to, fluoroscopy, x-ray, and MRI.

FIGS. 6a-6d illustrate a partial cross-sectional view of an exemplary incremental progression of a use of an exemplary device 200 for accurately controlling the extension of a needle from a protective sheath. Bi-directional control of device 200 is operated by retracting or extending sheath 208, respective to inner component assembly (which includes inner component 204, annular component 202, and needle 206) to cause ridge 202a of annular component 202 to engage one of slots 210 of sheath 208. Due to the flexible nature of sheath 208 compared to annular component 202, a user can overcome the frictional resistance of slot 210 by applying more force to, for example, inner handle component 204 or sheath 208. Indeed, it is contemplated that the materials may be reversed, thus having sheath 208 be more rigid than annular component 202. Once the initial resistance to movement is overcome, ridge 202a of annular component 202 will engage the next slot 210 of sheath 208, and it will remain locked there until enough force is applied to overcome the resistance. The retracting or extending of sheath 208 will cause sheath 208 to expose accurate portions of needle 206.

FIG. 6a illustrates device 200 in a fully un-retracted position wherein needle 206 is not exposed and is covered by sheath 208. When in the fully un-retracted position, annular component 202 and ridge 202a in particular, are disposed proximally of the proximal-most slot 210.

FIG. 6b illustrates sheath 208 partially retracted over inner component assembly causing ridge 202a of annular component 202 to engage with the first (proximal-most) slot 210 and thus accurately expose 2 mm of needle 206 from sheath 208.

FIG. 6c illustrates sheath 208 partially retracted over inner component assembly causing ridge 202a of annular component 202 to engage with the second slot 210 and thus accurately expose 4 mm of needle 206 from sheath 208.

FIG. 6d illustrates sheath 208 fully retracted over inner component assembly causing ridge 202a of annular component 202 to engage with the third slot 210 and thus accurately expose 6 mm of needle 206 from sheath 208.

The procedure illustrated in FIGS. 6a-6d can be repeated in whole or part to move sheath 208 distally or proximally respective to inner component assembly.

Slots 210 are illustrated as being spaced apart at increments of 2 mm such that when sheath 208 is retracted over inner component assembly, a length of 2 mm, 4 mm, or 6 mm of needle 206 is exposed from sheath 208. However, various other lengths of needle extension/exposure are contemplated, including but not limited to, those that are not at constant increments, such as 2 mm, 4 mm, 8 mm, or combination thereof. Indeed, more or less slots 210 are contemplated to provide various numbers of controlled needle extensions. By varying the number and spacing of slots 210, it is possible to have an infinite number of combinations of needle 206 extension length from sheath 208 for use in any type of treatment where a sheathed needled is desired, although not required.

FIG. 7 illustrates a partial cross-sectional view of an alternate embodiment of an exemplary device 700 for accurately controlling the extension of a needle from a protective sheath having proximal portion 700a, distal portion 700b, and handle as illustrated in FIG. 2a for connecting to an optional syringe. Sheath 704 has proximal portion 704a and distal portion 704b.

FIG. 8 illustrates a cross-sectional view of an exemplary outer sheath 704, and FIG. 9 illustrates a side view of an exemplary annular component 702 and needle 206. Sheath 704 has a sharp decrease of internal diameter which produces a concentric constriction, ridge 706. It is the interaction of ridge 706 with slots 702a of annular component 702 that provides accurate control of needle 206 extension.

As further illustrated in FIGS. 8-9, along with FIG. 7, within sheath 704 is annular component 702 having slots 702a that engage ridge 706 of sheath 704. Annular component 702 is attached to inner component 204 which attaches to flexible needle 206, or is formed monolithically with the needle 206. Alternatively, annular component 702 may attach directly to the flexible needle 206.

FIGS. 10a-10d illustrate a partial cross-sectional view of an exemplary incremental progression of a use of an exemplary device 700 for accurately controlling the extension of a needle from a protective sheath. Bi-directional control of device 700 is operated by retracting or extending sheath 704 using, for example, inner component assembly (which includes inner component 204, annular component 702, and needle 206), to cause one of slots 702a of annular component 702 to engage ridge 706 of sheath 704. Due to the flexible nature of sheath 704 compared to annular component 702, a user can overcome the frictional resistance of ridge 706 by applying more force to, inner handle component 204. Indeed, it is contemplated that the materials may be reversed, thus having sheath 704 be more rigid than component 702. Once the initial resistance to movement is overcome, the next slot 702a of annular component 702 will engage ridge 706 of sheath 704, and it will remain locked there until enough force is applied to overcome the resistance. The retracting or extending of sheath 704 will cause sheath 704 to expose accurate portions of needle 206.

FIG. 10a illustrates device 700 in a fully un-retracted position wherein needle 206 is not exposed and is covered by sheath 704. When in the fully un-retracted position, annular component 702 is disposed proximally of the ridge 706.

FIG. 10b illustrates sheath 704 partially retracted over inner component assembly causing first slot 702a of annular component 702 to engage with ridge 706 and thus accurately expose 2 mm of needle 206 from sheath 704.

FIG. 10c illustrates sheath 704 partially retracted over inner component assembly causing second slot 702a of annular component 702 to engage with ridge 706 and thus accurately expose 4 mm of needle 206 from sheath 704.

FIG. 10d illustrates sheath 704 fully retracted over inner component assembly causing third slot 702a of annular component 702 to engage with ridge 706 and thus accurately expose 6 mm of needle 206 from sheath 704.

The procedure illustrated in FIGS. 10a-10d can be repeated in whole or part to move sheath 704 proximally or distally with respect to inner component assembly distally.

Slots 702a of annular component 702 are illustrated as being spaced apart at increments of 2 mm such that when sheath 704 is retracted over inner component assembly, a length of 2 mm, 4 mm, or 6 mm of needle 206 is exposed from sheath 704. However, various other lengths of needle extension/exposure are contemplated, including but not limited to, those that are not at constant increments, such as 2 mm, 3 mm, 5 mm, or combination thereof. Indeed, more or less slots 702a of annular component 702 are contemplated to provide various numbers of controlled needle extensions. By varying the number and spacing of slots 702a of annular component 702, it is possible to have an infinite number of combinations of needle 206 extension length from sheath 704 for use in any type of treatment where a sheathed needled is desired, although not required.

FIG. 11 illustrates a partial cross-sectional view of an alternate embodiment of an exemplary device 1100 for accurately controlling the extension of a needle from a protective sheath having proximal portion 1100a, distal portion 1100b, and handle as illustrated in FIG. 2a for connecting to an optional syringe. Sheath 1104 has proximal portion 1104a and distal portion 1104b.

Figure 12:
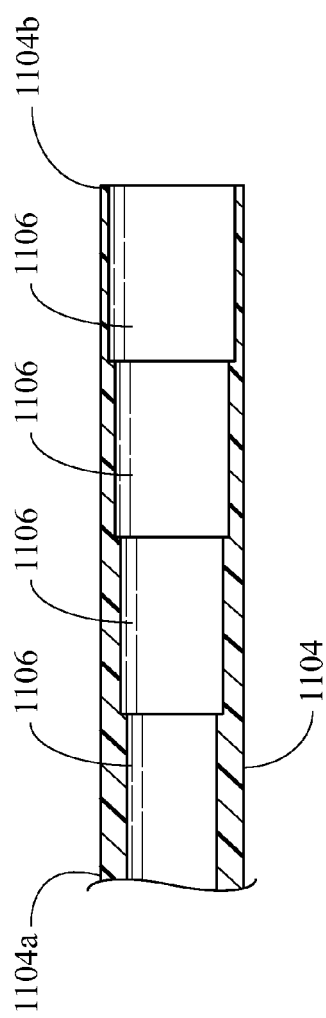
FIG. 12 illustrates a cross-sectional side view of an exemplary outer sheath.
Figure 13:
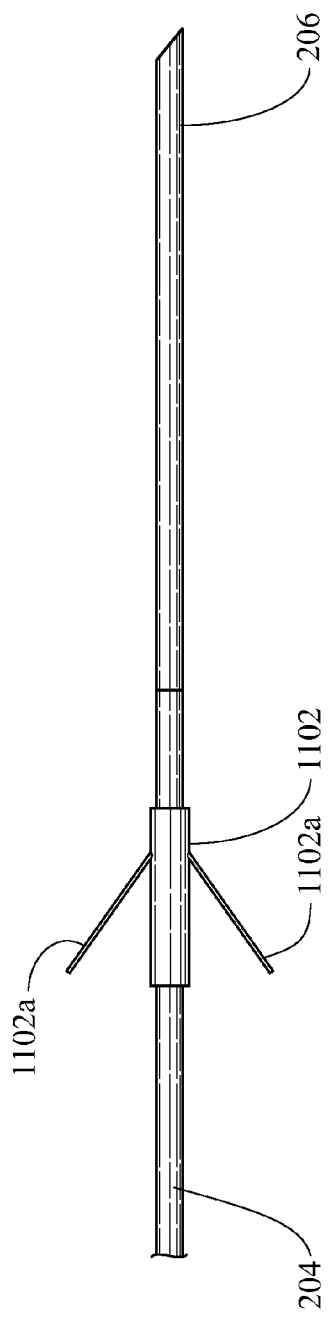
FIG. 13 illustrates a side view of an exemplary annular component and needle.

FIG. 12 illustrates a cross-sectional view of an exemplary outer sheath 1104, and FIG. 13 illustrates a side view of an exemplary annular component 1102 and needle 206. As further illustrated in FIGS. 12-13, along with FIG. 11, within sheath 1104 is annular component 1102 having wings 1102a that engage varying inner diameters 1106 of sheath 1104. Annular component 1102 is attached to inner component 204 which attaches to flexible needle 206.

Figure 14E:
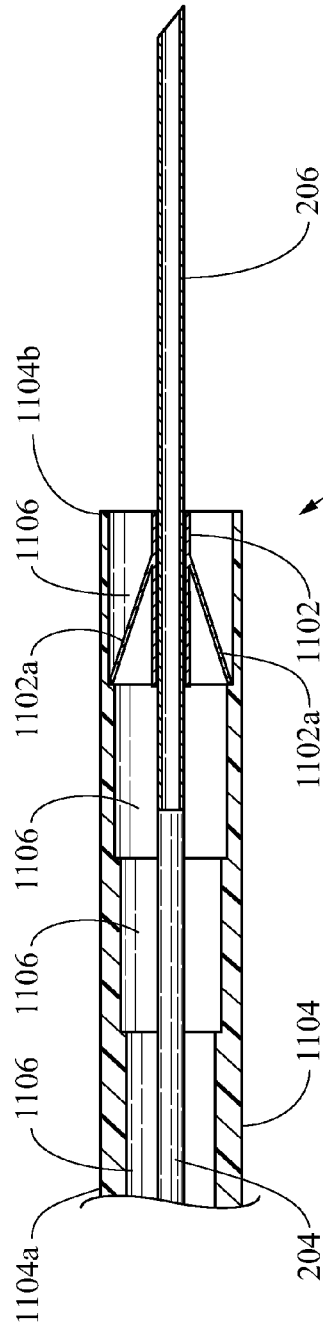

FIGS. 14a-14e illustrate a partial cross-sectional view of an exemplary incremental progression of a use of an exemplary device 1100 for accurately controlling the extension of a needle from a protective sheath. FIG. 14a illustrates device 1100 in a fully un-retracted position wherein needle 206 is not exposed and is covered by sheath 1104. Spring component wings 1102a are in a relaxed state whereby the wingspan of wings 1102a is greater that the diameter of sheath 1104. Control of device 1100 is operated by retracting sheath 1104, using, for example, inner component assembly (which includes inner component 204, annular component 1102, and needle 206) causing wings 1102a of annular component 1102 to compress due to the step change of varying inner diameters 1106 of sheath 1104. Due to the flexible compression nature of wings 1102a compared to sheath 1104, a user can overcome the frictional resistance of wings 1102a by applying more force to, for example, inner handle component 204. Indeed, it is contemplated that the materials may be reversed, thus having sheath 1104 be more rigid than wings 1102a. Once the initial resistance to movement is overcome, the next varying inner diameter 1106 of sheath 1104 will engage wings 1102a of annular component 1102, and it will remain locked there until enough force is applied to overcome the resistance because the spring component wings 1102a wingspan increases as sheath 1104 is further retracted. The retracting of sheath 1104 will cause sheath 1104 to expose accurate portions of needle 206.

FIG. 14a illustrates sheath 1104 fully un-retracted over inner component assembly. When in the fully un-retracted position, annular component 1102 is disposed proximally of the proximal-most varying inner diameter 1106.

FIG. 14b illustrates sheath 1104 partially retracted over inner component assembly causing first varying inner diameter 1106 of sheath 1104 to engage wings 1102a of annular component 1102 and not exposing any distal portion of needle 206.

FIG. 14c illustrates sheath 1104 partially retracted over inner component assembly causing second varying inner diameter 1106 of sheath 1104 to engage wings 1102a of annular component 1102 and thus accurately expose 2 mm of needle 206 from sheath 1104.

FIG. 14d illustrates sheath 1104 partially retracted over inner component assembly causing third varying inner diameter 1106 of sheath 1104 to engage wings 1102a of annular component 1102 and thus accurately expose 4 mm of needle 206 from sheath 1104.

FIG. 14e illustrates sheath 1104 fully retracted over inner component assembly causing fourth varying inner diameter 1106 of sheath 1104 to engage wings 1102a of annular component 1102 and thus accurately expose 6 mm of needle 206 from sheath 1104.

Varying inner diameters 1102a of annular component 1102 are illustrated as being spaced apart at increments of 2 mm such that when sheath 1104 is retracted over inner component assembly, a length of 2 mm, 4 mm, or 6 mm of needle 206 is exposed from sheath 1104. However, various other lengths of needle extension/exposure are contemplated, including but not limited to, those that are not at constant increments, such as 2 mm, 3 mm, 5 mm, or combination thereof. Indeed, more or less varying inner diameters 1106 of sheath 1104 are contemplated to provide various numbers of controlled needle extensions. By varying the number and spacing of varying inner diameters 1106 of sheath 1104, it is possible to have an infinite number of combinations of needle 206 extension length from sheath 1104 for use in any type of treatment where a sheathed needled is desired, although not required.

Furthermore, the step changes of varying inner diameters 1106 of sheath 1104 compresses spring components wings 1102a such that it is not possible to advance sheath 1104 in a distal direction to re-sheath needle 206. To overcome that, optional retraction mechanisms can be added to device 1100.

Figure 15:
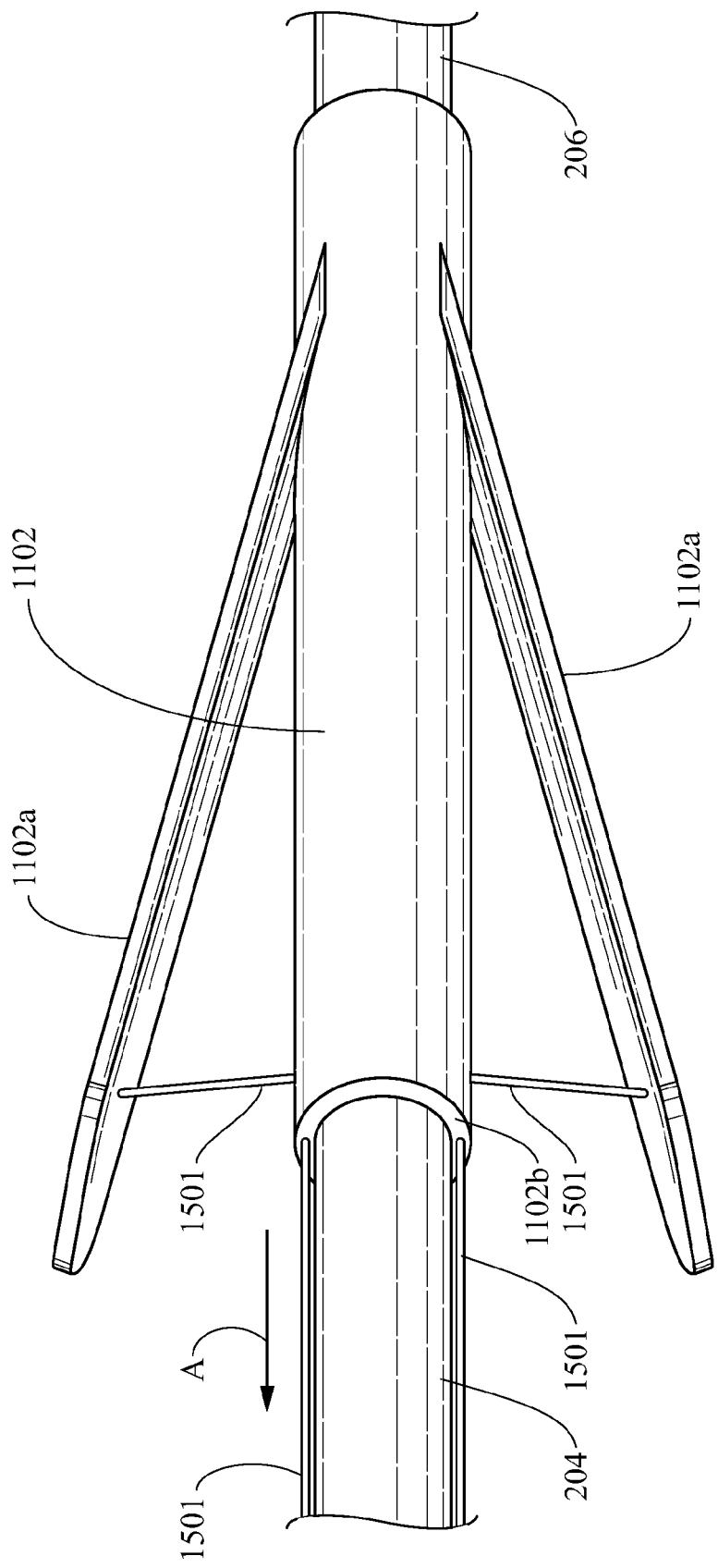
FIG. 15 illustrates a perspective view of an exemplary alternate annular component.

FIG. 15 illustrates a perspective view of an exemplary alternate annular component. Annular component 1102 further includes retrieval loop 1501 that threads from wings 1102a through body of annular component 1102b and along inner component 204 out to a user's hand or other control mechanism. To advance sheath 1104 over needle 206, user pulls retrieval loop 1501 in the direction of Arrow A causing wings 1102a to compress smaller than varying inner diameters 1106 and permit sheath 1104 to be extended over needle 206.

Figure 16:
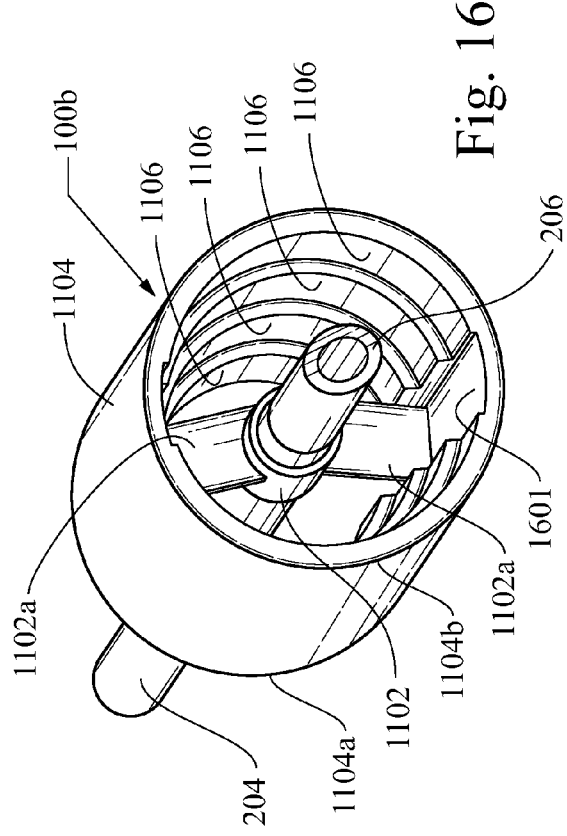
FIG. 16 illustrates a perspective view of an exemplary alternate sheath.

FIG. 16 illustrates a front view of an exemplary alternate sheath having retrieval slot 1601. To advance sheath 1104 over needle 206, user rotates needle 206 such that wings 1102a are in communication with retrieval slot 1601 permitting sheath 1104 to be extended over needle 206 such that wings 1102a slide axially within retrieval slot 1601. Handle channel 214 would be configured with, for example, a wider slot or additional slot, such that needle 206 or sheath 1104 would be rotatable respective to the other.

From the foregoing, it can be seen that the present disclosure provides devices that result in an accurate injection depth of a sheath covered flexible needle. The improved accuracy provides the user with more control over the device used and improves the outcome of the treatment procedure.

What is claimed is:
1. A medical device comprising:
  a needle comprising a proximal portion and a distal portion, wherein the distal portion of the needle comprises a sharpened tip;
  a sheath comprising a proximal portion, a distal portion, and a lumen extending between the proximal portion and the distal portion of the sheath, the lumen being defined by an inner surface of the sheath, wherein at least a portion of the needle is movably disposed through the lumen of the sheath;
a plurality of spaced apart first engagement members affixed to the inner surface of the sheath, comprising at least one change in an inner diameter between neighboring first engagement members;
a second engagement member affixed to the proximal portion of the needle, and comprises an annular component with at least one wing disposed about an outer surface of the annular component, wherein the wing of the annular component is configured to engage the at least one change in the inner diameter of the plurality of spaced apart first engagement members.

2. The medical device of claim 1, further comprising a handle in communication with the sheath, where the handle is configured for axial retraction or extension of the sheath to expose or conceal the distal portion of the needle.

3. The medical device of claim 1
wherein the wing of the annular component is configured to frictionally engage the first engagement members.

4. The medical device of claim 1, wherein the at least one change in the inner diameter of the plurality of spaced apart first engagement members further comprises:
a first change in inner diameter;
a second change in inner diameter; and
a third change in inner diameter;
wherein the first change in inner diameter comprises a diameter smaller than a diameter of the second and third changes in inner diameter, wherein the second change in inner diameter comprises a diameter larger than the first change in inner diameter, and wherein the third change in inner diameter comprises a diameter larger than the second change in inner diameter.

5. The medical device of claim 4, wherein the first change in inner diameter, second change in inner diameter, and third change in inner diameter each traverse a length of the sheath along a longitudinal axis of the sheath.

6. The medical device of claim 5, wherein each of the first, second, and third changes in inner diameter traverse a different length of the sheath along the longitudinal axis.

7. The medical device of claim 1, wherein the annular component further comprises a retrieval loop comprising a proximal portion and a distal portion, wherein the distal portion is attached to the at least one wing of the annular component, and wherein the retrieval loop is configured to compress the at least one wing of the annular component when the proximal portion of the retrieval loop is pulled.

8. The medical device of claim 1, wherein the sheath further comprises a retrieval slot disposed about an inner surface of the sheath, wherein the retrieval slot is configured to slideably engage the at least one wing of the annular component.

9. The medical device of claim 1, wherein the proximal portion of the needle is sufficiently flexible such that angulation of an endoscope is not unduly diminished or hindered when disposed through a working channel of the endoscope.

10. The medical device of claim 1, wherein each of the first engagement members are cylindrical.

11. The medical device of claim 1, wherein the annular component comprises two wings.

12. The medical device of claim 1, wherein the at least one change in diameter between neighboring first engagement members defines a step upon an end of a portion of the inner surface of the sheath with the smaller diameter of the at least one change in diameter, wherein the wing of the annular component engages the step when the sheath is urged toward the distal end of the needle, which prevents distal motion of the sheath with respect to the needle.

13. A medical device comprising:
a needle comprising a proximal portion and a distal portion, wherein the distal portion of the needle comprises a sharpened tip;
a sheath comprising a proximal portion, a distal portion, and a lumen extending between the proximal portion and the distal portion of the sheath, the lumen being defined by an inner surface of the sheath, wherein at least a portion of the needle is movably disposed through the lumen of the sheath,
wherein the inner surface of the sheath further comprises at least one change in a diameter between neighboring portions of the sheath;
an annular component disposed around a portion of a surface of the needle, wherein the annular component further comprising at least one wing disposed about an outer surface of the annular component,
wherein the winq of the annular component is configured to incrementally engage the change in the diameter of the inner surface of the sheath; and
a handle attached to the sheath and the needle, where the handle is configured for axial retraction and extension of the sheath to incrementally engage the annular component and expose or conceal a distal portion of the needle.

14. The medical device of claim 13, wherein the needle further comprises at least one marker, wherein the marker is configured for visualization by a direct or indirect visualization device.

15. The medical device of claim 13, further comprising a connector connected to a proximal portion of the handle, wherein the connector is configured to receive a syringe.

16. The medical device of claim 13, wherein the proximal portion of the needle is sufficiently flexible such that angulation of an endoscope is not unduly diminished or hindered when disposed through a working channel of the endoscope.

17. The medical device of claim 13, wherein the at least one change in diameter between neighboring portions of the inner surface of the sheath defines a step upon an end of a portion of the inner surface of the sheath with the smaller diameter of the at least one change in diameter, wherein the wing of the annular component engages the step when the sheath is urged toward the distal end of the needle, which prevents distal motion of the sheath with respect to the needle.

18. A medical device comprising:
a needle comprising a proximal portion and a distal portion, wherein the distal portion of the needle comprises a sharpened tip;
a sheath comprising a proximal portion, a distal portion, and a lumen extending between the proximal portion and the distal portion of the sheath, the lumen being defined by an inner surface of the sheath, wherein at least a portion of the needle is movably disposed through the lumen of the sheath;
a first accurate needle extension member in communication with the inner surface of the sheath comprising at least one change in a diameter between neighboring portions of the inner surface of the sheath; and
a second accurate needle extension member in communication with the needle, wherein the second extension member comprises an annular component comprising at least one wing disposed about an outer surface of the annular component,
wherein the wing of the second accurate needle extension member is configured for engagement with the change in the diameter of the first accurate needle extension member for accurately extending a length of the needle from the distal portion of the sheath.

19. The medical device of claim 18, wherein the at least one change in diameter between neighboring portions of the inner surface of the sheath defines a step upon an end of a portion of the inner surface of the sheath with the smaller diameter of the at least one change in diameter, wherein the wing of the annular component engages the step when the sheath is urged toward the distal end of the needle, which prevents distal motion of the sheath with respect to the needle.

* * * * *

UNITED STATES PATENT AND TRADEMARK OFFICE
CERTIFICATE OF CORRECTION

Page 1 of 1

PATENT NO. : 9,216,258 B2
APPLICATION NO. : 13/441368
DATED : December 22, 2015
INVENTOR(S) : Paul David Devereux et al.

It is certified that error appears in the above-identified patent and that said Letters Patent is hereby corrected as shown below:

In the Claims

In column 11, claim 4, line 24, after "change in the inner diameter" replace "of" with --between--.

Signed and Sealed this
Twelfth Day of April, 2016

Michelle K. Lee
*Director of the United States Patent and Trademark Office*